United States Patent [19]

Shieh et al.

[11] Patent Number: 5,708,259
[45] Date of Patent: Jan. 13, 1998

[54] MICROWAVE DECOMPOSITION MACHINE WITH OUTPUT DOOR MECHANISM

[75] Inventors: Yuh-Ren Shieh; Chi-non Chen; Jey-cherng Chen; Chun-yuh Yu, all of Hsinchu, Taiwan

[73] Assignee: Industrial Technology Research Institute, Hsin-Chu, Taiwan

[21] Appl. No.: 428,764

[22] Filed: Apr. 24, 1995

Related U.S. Application Data

[62] Division of Ser. No. 239,291, May 6, 1994, Pat. No. 5,429,799.

[51] Int. Cl.$^6$ .............................. H05B 6/76; H05B 6/78
[52] U.S. Cl. .......................... 219/738; 219/739; 219/741; 219/762; 333/261; 174/35 GC
[58] Field of Search ............................. 219/738, 741, 219/742, 743, 679, 695, 762, 739; 333/261; 174/35 GC, 35 MS; 422/21

[56] References Cited

U.S. PATENT DOCUMENTS

| | | | |
|---|---|---|---|
| 2,751,559 | 6/1956 | McCann et al. | 333/261 |
| 3,229,234 | 1/1966 | Lattanzi | 333/261 |
| 3,424,853 | 1/1969 | Johnson, III | 333/261 |
| 3,531,577 | 9/1970 | Garlington | 174/35 GC |
| 4,370,534 | 1/1983 | Brandon | 219/695 |
| 4,778,970 | 10/1988 | Klaila | 219/695 |
| 4,975,246 | 12/1990 | Charm | 422/21 |
| 5,003,143 | 3/1991 | Marks et al. | 219/10.55 |
| 5,124,125 | 6/1992 | Brent | 422/21 |
| 5,191,184 | 3/1993 | Shin | 219/10.55 |
| 5,196,069 | 3/1993 | Cullingford et al. | 127/37 |
| 5,209,902 | 5/1993 | Matthews et al. | 422/21 |
| 5,213,758 | 5/1993 | Kawashima et al. | 422/21 |
| 5,223,231 | 6/1993 | Drake | 422/297 |
| 5,237,938 | 8/1993 | Fujimori et al. | 110/240 |

*Primary Examiner*—Philip H. Leung
*Attorney, Agent, or Firm*—George O. Saile; Larry J. Prescott

[57] ABSTRACT

An output door mechanism for a microwave decomposition machine allows a rotating tank to be coupled to a fixed waveguide with both a vacuum and a microwave seal. The fixed waveguide delivers microwave power to the rotating tank in a decomposition machine. A moveable end cover joins the rotating tank to the fixed waveguide providing the rotating tank with a vacuum and microwave seal during the decomposition of material and discharge of the tank after the decomposition has been completed. The output door mechanism uses a rolling bearing to form a rolling seal, a sliding bearing to form a sliding seal, and a metallic bellows to form a flexible seal. A plunger compresses a spring to seal the end cover to the rotating tank. When the plunger no longer applies compressive force to the spring the end cover separates from the rotating tank to allow discharge of the decomposed material.

5 Claims, 2 Drawing Sheets

MICROWAVE DECOMPOSITION MACHINE WITH OUTPUT DOOR MECHANISM

This is a Divisional patent application of Ser. No. 08/239, 291, filed May 6, 1994, now U.S. Pat. No. 5,429,799.

BACKGROUND OF THE INVENTION

(1) Field of the Invention

The invention relates to the decomposition and sterilization of medical waste material and more particularly to the treatment of medical waste material with microwave energy in an inert atmosphere prior to disposal.

(2) Description of the Related Art

The problem of disposing of medical waste material is a serious problem which is getting more and more serious as time goes on. Medical waste material must be properly treated before being disposed of in order to insure that soil or water supplies around dumping grounds or landfill areas will not become contaminated with dangerous organisms. Incineration of medical waste material, which has long been an important method of treating medical waste, must be carried out with great care to prevent discharge of dangerous waste material into the atmosphere. Along with need for methods which will handle medical waste material safely is the need to handle such material economically.

A number of methods for dealing with medical waste material have been patented. A number of these patents describe the use of microwave energy to heat the waste material often in conjunction with other types of processing, for example Robert C. Drake in U.S. Pat. No. 5,223,231 or Norihiro Kawashima et al in U.S. Pat. No. 5,213,758. Minoru Fujimori et al in U.S. Pat. No. 5,237,938 describe an incinerator with a main burner into which a mixture of oil and water are injected to incinerate the medical waste material.

During the decomposition and sterilization of the medical waste material care must be taken to avoid discharging dangerous gases into the atmosphere. If microwave energy is used to heat medical waste material care must be taken to avoid waste material causing arcing in the vicinity of the rotary tank.

SUMMARY OF THE INVENTION

It is a principle object of this invention to provide a machine which will safely decompose and sterilize medical waste material so that the decomposed and sterilized residue can be disposed of by conventional means.

It is a further object of this invention to provide a method which will safely decompose and sterilize medical waste material so that the decomposed and sterilized residue can be disposed of by conventional means.

It is a further object of this invention to provide a means to decompose, sterilize, and dispose of medical waste material economically and in a manner that will not expel dangerous material into either the atmosphere, ground or water supply.

These objectives are achieved by means of a machine which shreds medical waste material into strips of between about 10 to 20 cm in length with a width or diameter of less than about 2.5 cm and uses microwave energy in a sealed atmosphere to decompose and sterilize the medical waste material. The machine has a capability to provide a sealed atmosphere during the decomposition and sterilization process thereby preventing the discharge of any medical waste solids or gases into the atmosphere. The sealed atmosphere also makes it possible to prevent the leakage of oxygen from the outside atmosphere during the decomposition and sterilization process. The decomposed and sterilized medical waste gases are collected in a gas condenser attached to the machine. The solid decomposed and sterilized medical waste material can be discharged into a trolly to be removed for conventional disposal.

The sealed atmosphere is accomplished by means of an output door which forms a rotary joint between a fixed waveguide and a rotary tank. This output door forms a vacuum seal and a microwave energy seal between the fixed waveguide and rotary tank. The output door also provides a means to discharge solid decomposed and sterilized medical waste material from the rotary tank.

First, an inert gas such as nitrogen or carbon dioxide is introduced into the tank to purge and expel the air inside the rotary tank. Then, the medical waste material is shredded and introduced into the rotary tank. A microwave generator generates microwave energy which is introduced into the rotary tank by means of a waveguide. Since the mixing blade is attached to the rotary tank containing the medical waste material particles there will not be arcing or other undesirable effects in the rotary tank. The microwave energy decomposes and sterilizes the medical waste material in the rotary tank. Gases generated during the decomposition and sterilization process are collected in a gas condenser. The microwave generator is then turned off, the output door between the rotary tank and the waveguide is opened and the solid decomposed and sterilized medical waste material is discharged from the rotary tank into a trolly for removal.

The machine can be mounted on a vehicle and transported to the source of the medical waste material such as a hospital, physician's office, dentist's office, etc.

DESCRIPTION OF THE PREFERRED EMBODIMENTS

Figure 1:
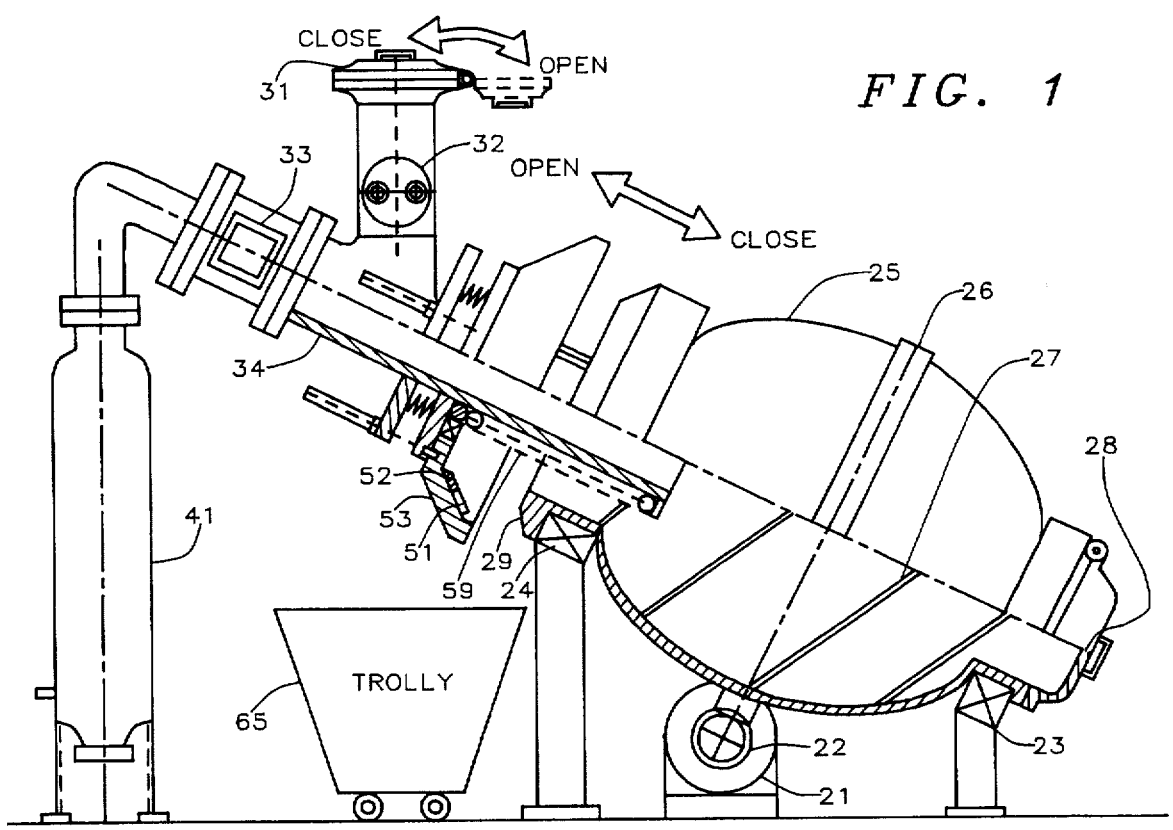
FIG. 1 is a cross sectional representation of the microwave decomposition machine.
Figure 2:
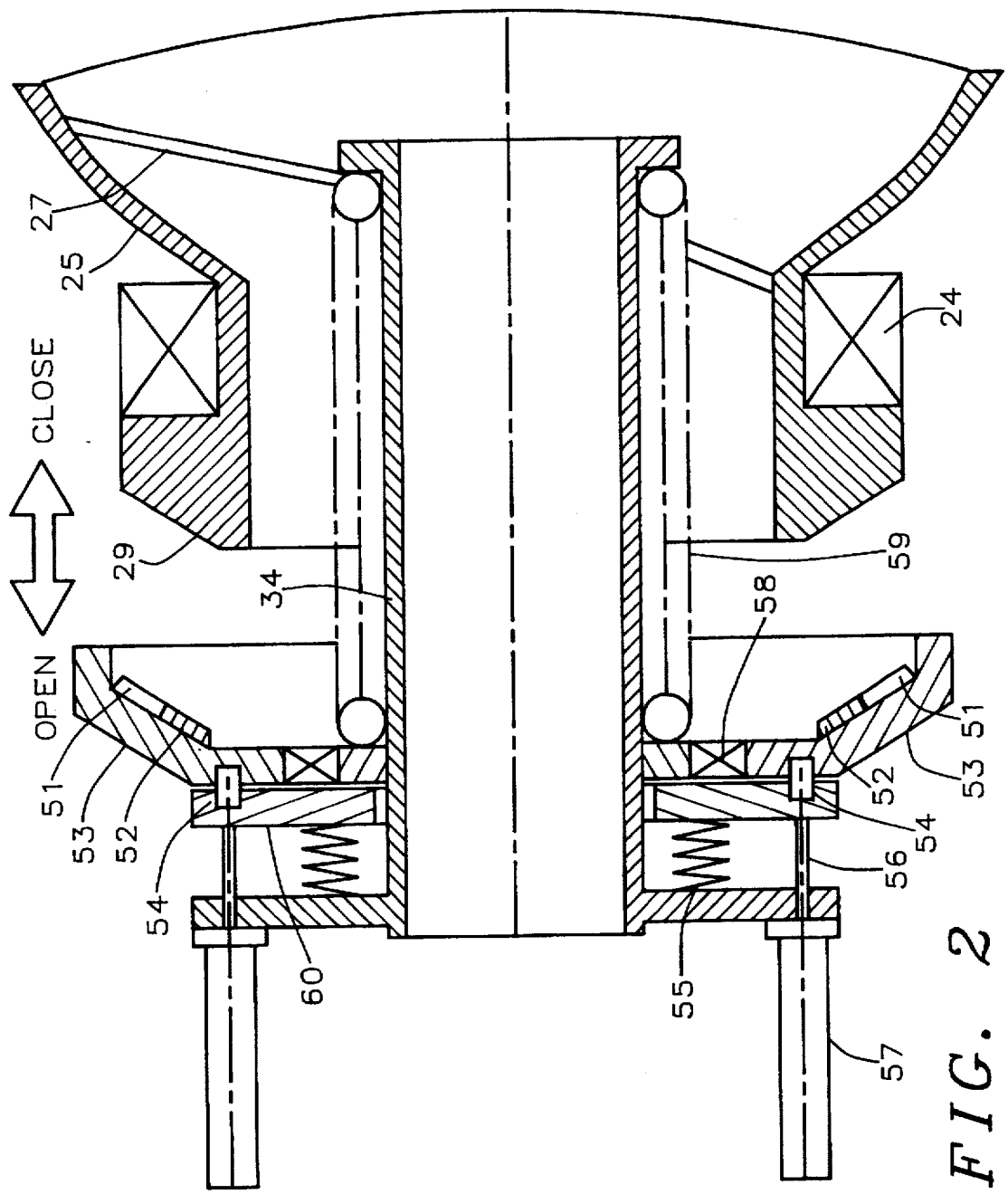
FIG. 2 is a cross sectional representation of the output door which serves as a rotary joint between the fixed waveguide and the rotary tank.

An embodiment of the microwave decomposition machine is shown in FIG. 1. The principle parts of the machine are an input door 31, shredder 32, a microwave generator 33, a waveguide 34, a rotary tank 25, a gas condenser 41, and an output door mechanism. Refer to FIG. 2 where the output door mechanism is shown. The principle parts of the output door mechanism are the end cover 53; the plunger plate 60; the rubber gasket 51, such as a viton sealing gasket; the metallic mesh gasket 52, such as a stainless steel or copper mesh gasket; the sliding bearing 54, such as a graphite sliding bearing; the rolling bearing 58; the metallic bellows 55; the plunger 56; the actuator 57; and the compression spring 59.

Refer now to FIGS. 1 and 2 for the embodiment of the method of decomposition and sterilization of medical waste material. At the beginning of the decomposition and sterilization cycle the output door is closed forming both a vacuum seal and a microwave energy seal between the fixed waveguide and the rotary tank. Refer now more particularly to FIG. 2 which shows a cross sectional view of the output door. When the output door is closed the actuator 57 and the plunger 56 pushing on the plunger plate 60 force the end cover 53 in place against the sealing face 29 of the rotary tank 25 thereby compressing the compression spring 59. The rubber gasket 51 and the metallic mesh gasket 52 are compressed against the rotary tank sealing face 29 to form a gas tight seal and a microwave energy seal respectively. The rolling bearing 58 separates the end cover from the fixed waveguide 34 and allows the end cover to rotate with respect to the fixed waveguide. Any gas which escapes through the rolling bearing 58 is prevented from escaping into the atmosphere by the metallic bellows 55 and by the graphite sliding bearing 54 between the end cover 53 and the plunger plate 60.

Refer now to FIG. 1 where is shown a cross sectional view of the microwave decomposition machine. At the beginning of the decomposition cycle the medical waste material to be treated is introduced through the input door 31. Then the input door 31 is closed and an inert gas such as nitrogen, carbon dioxide or the like (to keep oxygen less than about 1%) is introduced into the interior of the decomposition machine through a valve 28 at the end of the rotary tank to purge the air inside. The output door is then closed as described above. The medical waste material is then shredded by the shredder 32 into strips of varying length, up to about 10 to 20 cm, with a width or diameter of less than about 2.5 cm. The shredded waste material then falls to the interior of the fixed waveguide 34 and from the fixed waveguide into the interior of the rotary tank 25 coming to rest against the helical mixing blades 27 attached to the inner surface of the rotary tank.

Next the microwave generator 33 generates microwave energy of about 60 Kilowatts which travels down the fixed waveguide 34 and into the interior of the rotary tank 25. The microwave generator may be chosen to be 915 MHz or 2450 MHz. The preferred frequency is 915 MHz because the generator is currently available and less expensive. The driving motor 21, worm gear 22 and gear ring 26 cause the rotary tank 25 to rotate while being supported by bearings 23, 24, and 58. The helical mixing blades 27 continually stir the shredded medical waste material particles which are decomposed and sterilized by the microwave energy.

The decomposition and sterilization process occurs in an oxygen free atmosphere inside the rotary tank. Any gases which are generated during the decomposition process are collected by the gas condenser 41 to be further recycled. The machine is completely sealed during the decomposition and sterilization process so no gaseous waste is discharged into the atmosphere. The gas condenser 41 may also be equipped with a disinfection device such as an ultraviolet light source.

Refer again to FIG. 2. At the completion of the decomposition cycle the microwave generator is turned off and the rotation of the rotary tank is reversed. The output door is opened by moving the end cover 53 away from the rotary tank 25.

Refer again to FIG. 1. With the rotation direction of the rotary tank 25 reversed; being driven by the driving motor 21, the worm gear 22, and the gear ring 26; the helical mixing blade 27 moves the decomposed and sterilized solid medical waste material out of the output door and into the trolly 65 for safe disposal. The microwave decomposition machine is then ready for the next batch of medical waste material.

Another embodiment of the invention consists of the microwave decomposition machine mounted on a truck or other suitable vehicle. The truck then transports the microwave decomposition machine to the source of the medical waste material such as a hospital, physician's office, dentist's office, etc. The microwave decomposition machine then processes the medical waste material as previously described and transports the microwave decomposition machine to the next source of medical waste material.

While the invention has been particularly shown and described with reference to the preferred embodiments thereof, it will be understood by those skilled in the art that various changes in form and details may be made without departing from the spirit and scope of the invention.

What is claimed is:

1. An output door mechanism forming a rotary joint between a rotary tank and a fixed waveguide, comprising:

a fixed waveguide;

a rotary tank, wherein said rotary tank can be rotated relative to said fixed waveguide;

a moveable end cover joining said rotary tank to said fixed waveguide, wherein said end cover rotates with said rotary tank relative to said fixed waveguide;

a vacuum sealing gasket between said end cover and said rotary tank, wherein said vacuum sealing gasket can provide a gas tight seal between said end cover and said rotary tank;

a microwave sealing gasket between said end cover and said rotary tank, wherein said microwave sealing gasket can provide a microwave energy seal between said end cover and said rotary tank;

a rolling bearing forming a rolling seal between said fixed waveguide and said end cover;

a sliding bearing forming a sliding seal between said fixed waveguide and said end cover;

a metallic bellows forming a flexible seal between said end cover and said fixed waveguide, wherein said rolling bearing, said sliding bearing, and said metallic bellows form a gas tight seal between said end cover and said fixed waveguide; and a means for moving said moveable end cover.

2. The mechanism of claim 1 wherein said vacuum sealing gasket is rubber.

3. The mechanism of claim 1 wherein said microwave sealing gasket is stainless steel mesh or copper mesh.

4. The mechanism of claim 1 wherein said sliding bearing is a graphite bearing.

5. The mechanism of claim 1 wherein said means for moving said movable end cover further comprises:

a plunger to force said end cover against said rotary tank;

a spring between said movable end cover and said fixed waveguide wherein said spring is compressed when said end cover is forced against said rotary tank; and an actuator to move said plunger.

* * * * *